US012605284B2

(12) United States Patent
Stewart et al.

(10) Patent No.: US 12,605,284 B2
(45) Date of Patent: Apr. 21, 2026

(54) AUTOMATIC DARKENING APPARATUS WITH INTEGRATED MAGNIFICATION LENS

(71) Applicant: Lincoln Global, Inc., Santa Fe Springs, CA (US)

(72) Inventors: Eric G. Stewart, Girard, PA (US); Paul H. Rumpke, Lakewood, OH (US)

(73) Assignee: LINCOLN GLOBAL, INC., Santa Fe Springs, CA (US)

( * ) Notice: Subject to any disclaimer, the term of this patent is extended or adjusted under 35 U.S.C. 154(b) by 852 days.

(21) Appl. No.: 17/859,134

(22) Filed: Jul. 7, 2022

(65) Prior Publication Data

US 2024/0009034 A1      Jan. 11, 2024

(51) Int. Cl.
*A61F 9/06*          (2006.01)
*G02B 25/00*          (2006.01)

(52) U.S. Cl.
CPC ............ *A61F 9/067* (2013.01); *G02B 25/002* (2013.01)

(58) Field of Classification Search
CPC .............................. A61F 9/067; G02B 25/002
USPC ......................................................... 359/614
See application file for complete search history.

(56) References Cited

U.S. PATENT DOCUMENTS

| | | | | |
|---|---|---|---|---|
| 2,230,369 | A | * | 2/1941 | Wise ....................... C03C 17/22 |
| | | | | 359/581 |
| 5,825,441 | A | | 10/1998 | Hörnell et al. |
| 6,097,451 | A | | 8/2000 | Palmer et al. |
| 6,230,327 | B1 | | 5/2001 | Briand et al. |
| 7,477,330 | B2 | | 1/2009 | Magnusson et al. |
| 8,438,663 | B2 | | 5/2013 | Wright |
| 9,073,138 | B2 | | 7/2015 | Wills et al. |

(Continued)

FOREIGN PATENT DOCUMENTS

| | | |
|---|---|---|
| CN | 87 2 16198 U | 9/1988 |
| WO | 2021/149942 A1 | 7/2021 |
| WO | 2021245609 A1 | 12/2021 |

OTHER PUBLICATIONS

3M; "3M Speedglas Welding Safety Product Catalog 2012/2013;" https://spec-sheets.interlinksupply.com/77622_Catalog.pdf; Accessed on Mar. 24, 2022; pp. 1-68.

(Continued)

*Primary Examiner* — Bumsuk Won
*Assistant Examiner* — Mitchell T Oestreich
(74) *Attorney, Agent, or Firm* — David J. Muzilla; Ivan P. Gracic

(57)          ABSTRACT

An embodiment includes an auto-darkening apparatus for supporting welding performed by a human welder. The auto-darkening apparatus includes a housing configured to be removably installed into a welding helmet. The auto-darkening apparatus also includes an ADF lens assembly configured to transition from an un-darkened state to a darkened state in response to light from an arc being formed between a welding electrode and a work piece during a welding process. The auto-darkening apparatus further includes a magnification assembly integrated with the ADF lens assembly within the housing. The magnification assembly is configured to provide magnification of light coming through the ADF lens assembly. The magnification is continuously user-adjustable from a defined lower level of magnification to a defined upper level of magnification.

11 Claims, 8 Drawing Sheets

(56) References Cited

U.S. PATENT DOCUMENTS

| | | | |
|---|---|---|---|
| 9,889,045 | B2 | 2/2018 | Matthews et al. |
| 10,821,026 | B2 | 11/2020 | Magnusson et al. |
| 2006/0010551 | A1 | 1/2006 | Bishop et al. |
| 2007/0089215 | A1 | 4/2007 | Biche et al. |
| 2011/0285957 | A1 | 11/2011 | Mikulenka et al. |
| 2014/0007312 | A1* | 1/2014 | Wright .................... A61F 9/064 |
| | | | 2/8.2 |
| 2015/0320601 | A1 | 11/2015 | Gregg |
| 2015/0359679 | A1* | 12/2015 | Sommers ............... A42B 3/225 |
| | | | 2/8.5 |
| 2019/0125586 | A1 | 5/2019 | Magnusson et al. |
| 2023/0053923 | A1* | 2/2023 | Huh .......................... F16P 1/06 |

OTHER PUBLICATIONS

Extended European Search Report for Corresponding Application No. 23180625.8; Dated Dec. 18, 2023; pp. 1-30.

\* cited by examiner

AUTOMATIC DARKENING APPARATUS WITH INTEGRATED MAGNIFICATION LENS

REFERENCE

The disclosure of U.S. Pat. No. 5,825,441, issued on Oct. 20, 1998, is incorporated by reference herein in its entirety. The disclosure of U.S. Pat. No. 6,097,451, issued on Aug. 1, 2000, is incorporated by reference herein in its entirety. The disclosure of U.S. Pat. No. 7,477,330 B2, issued on Jan. 13, 2009, is incorporated by reference herein in its entirety. The disclosure of U.S. Pat. No. 9,889,045 B2, issued on Feb. 1, 2018, is incorporated by reference herein in its entirety.

FIELD

Embodiments of the present invention relate to automatic darkening filter assemblies for welding helmets. More specifically, embodiments of the present invention relate to automatic darkening filter assemblies for welding helmets having adjustable magnification capability.

BACKGROUND

Welding magnifiers (cheater lenses) are commonly used in welding helmets over top of the welding lens for both passive and auto darkening helmets. Such clear magnifiers can be bothersome to change in and out based on various welding conditions, are easily scratched and, in older welders, can cause double vision from stacking three lenses (i.e., a clear cover plate, a welding lens, and a magnifying lens).

SUMMARY

An embodiment includes an automatic darkening filter (ADF) housing having an ADF lens and a mechanically adjustable magnifying lens integrated therein. Magnifying strength may range from 1.00-3.00 magnification, for example, and is continuously adjustable in accordance with one embodiment. A welder is able to adjust the desired level of magnification without the need for a separate lens (without having to swap out one lens for another). The welder is able to adjust the magnification level up or down based on their liking for each welding application and limitations of near and far sightedness (i.e., restrictions in how close or far the welder's eyes are from the welding arc, the size of the welding arc, and small or large weld puddles).

One embodiment provides an auto-darkening apparatus for supporting welding performed by a human welder. The auto-darkening apparatus includes a housing configured to be removably installed into a welding helmet. The auto-darkening apparatus also includes an ADF lens assembly configured to transition from an un-darkened state to a darkened state in response to light from an arc being formed between a welding electrode and a work piece during a welding process. The auto-darkening apparatus further includes a magnification assembly integrated with the ADF lens assembly within the housing. The magnification assembly is configured to provide magnification of light coming through the ADF lens assembly. The magnification is continuously user-adjustable from a defined lower level of magnification to a defined upper level of magnification. In one embodiment, the defined lower level of magnification is a magnification level of 1 (i.e., no magnification). In one embodiment, the defined upper level of magnification is between 1.9 and 4.1. In one embodiment, the defined upper level of magnification is between 1.4 and 2.1. In one embodiment, the magnification assembly includes at least one optical magnifying lens. In one embodiment, the magnification assembly includes at least one convex optical lens. In one embodiment, the magnification assembly includes at least one concave optical lens. In one embodiment, the magnification assembly includes an optical lens configuration and a magnifying lens adjustment configured to be manipulated by a user to mechanically adjust an angle at which at least a portion of the optical lens configuration is oriented within the housing, resulting in an adjustment of a level of magnification of light coming through the ADF lens assembly as viewed by the user. In one embodiment, the magnification assembly includes an optical lens configuration and a magnifying lens adjustment configured to be manipulated by a user to mechanically adjust at least one of a focal length of the optical lens configuration or a position of at least a portion of the optical lens configuration within the housing, resulting in an adjustment of a level of magnification of light coming through the ADF lens assembly as viewed by the user. In one embodiment, the auto-darkening apparatus is configured to provide user adjustment of at least one of a sensitivity, a shade, and a delay of the ADF lens assembly.

One embodiment provides a welding helmet for supporting welding performed by a human welder. The welding helmet includes a helmet shell, having a viewing window, configured to be worn on the head of a user. The welding helmet also includes an ADF lens assembly, within a first housing, configured to transition from an un-darkened state to a darkened state in response to light from an arc being formed between a welding electrode and a work piece during a welding process. The first housing is configured to be removably attached to the helmet shell at the viewing window. The welding helmet further includes a magnification assembly, within a second housing, configured to provide magnification of light coming through the ADF lens assembly. The magnification is continuously user-adjustable from a defined lower level of magnification to a defined upper level of magnification. The second housing is configured to be removably attached to the helmet shell adjacent to the first housing at the viewing window. In one embodiment, the defined lower level of magnification is a magnification level of 1 (i.e., no magnification). In one embodiment, the defined upper level of magnification is between 1.9 and 4.1. In one embodiment, the defined upper level of magnification is between 1.4 and 2.1. In one embodiment, the magnification assembly includes at least one optical magnifying lens. In one embodiment, the magnification assembly includes at least one convex optical lens. In one embodiment, the magnification assembly includes at least one concave optical lens. In one embodiment, the magnification assembly includes an optical lens configuration and a magnifying lens adjustment configured to be manipulated by a user to mechanically adjust an angle at which at least a portion of the optical lens configuration is oriented within the second housing, resulting in an adjustment of a level of magnification of light coming through the ADF lens assembly as viewed by the user. In one embodiment, the magnification assembly includes an optical lens configuration and a magnifying lens adjustment configured to be manipulated by a user to mechanically adjust at least one of focal length of the optical lens configuration or a position of at least a portion of the optical lens configuration within the second housing, resulting in an adjustment of a level of magnification of light coming through the ADF lens assembly as viewed by the user. In one embodiment, the welding helmet is configured to provide user adjustment of at least one of a sensitivity, a shade, and a delay of the ADF lens assembly.

Numerous aspects of the general inventive concepts will become readily apparent from the following detailed description of exemplary embodiments, from the claims, and from the accompanying drawings.

BRIEF DESCRIPTION OF THE DRAWINGS

The accompanying drawings, which are incorporated in and constitute a part of the specification, illustrate various embodiments of the disclosure. It will be appreciated that the illustrated element boundaries (e.g., boxes, groups of boxes, or other shapes) in the figures represent one embodiment of boundaries. In some embodiments, one element may be designed as multiple elements or multiple elements may be designed as one element. In some embodiments, an element shown as an internal component of another element may be implemented as an external component and vice versa. Furthermore, elements may not be drawn to scale.

DETAILED DESCRIPTION

Figure 1A:
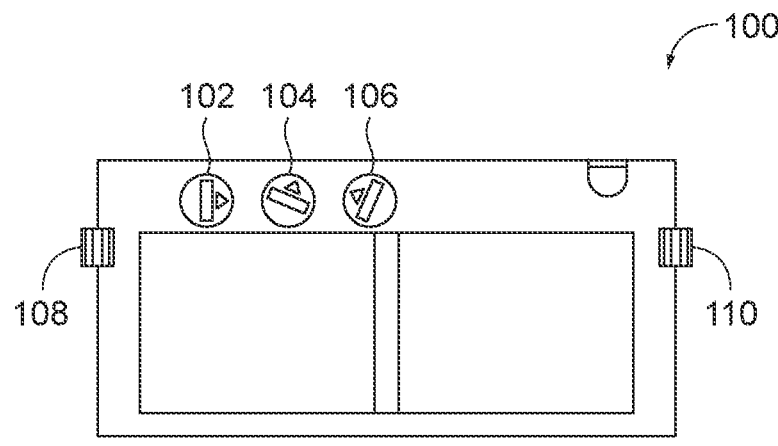
FIG. 1A, FIG. 1B, and FIG. 1C illustrates several views of one embodiment of an auto-darkening apparatus for supporting welding performed by a human welder.

One embodiment of the present invention includes an auto-darkening apparatus having an ADF lens assembly integrated with a magnification assembly within an ADF housing for use in a welding helmet. One embodiment of the present invention includes a welding helmet configured to have installed therein an auto-darkening apparatus having an ADF lens assembly integrated with a magnification assembly within an ADF housing. In one embodiment, the auto-darkening apparatus is in the form of a cartridge that removably snaps into the welding helmet.

The examples and figures herein are illustrative only and are not meant to limit the subject invention, which is measured by the scope and spirit of the claims. Referring now to the drawings, wherein the showings are for the purpose of illustrating exemplary embodiments of the subject invention only and not for the purpose of limiting same, FIG. 1A, FIG. 1B, and FIG. 1C illustrates several views of one embodiment of an auto-darkening apparatus 100 for supporting welding performed by a human welder.

Figure 1B:
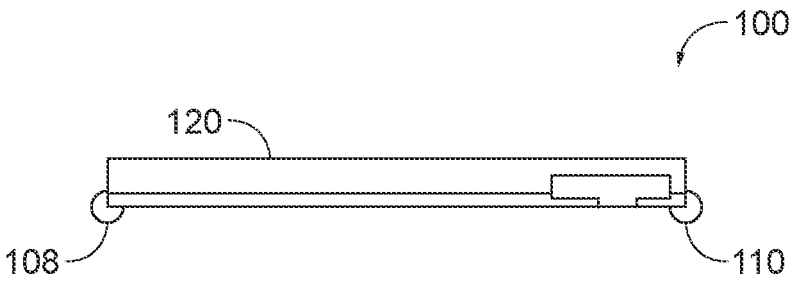
Figure 1C:
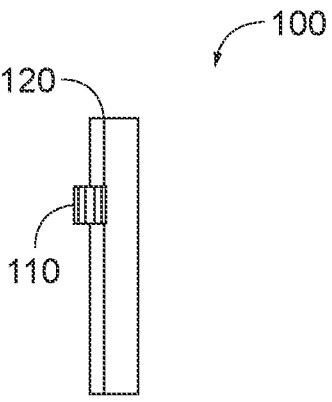

FIG. 1A is a rear view (as viewed by a user) of the auto-darkening apparatus 100, FIG. 1B is a top view of the auto-darkening apparatus 100, and FIG. 1C is a side view of the auto-darkening apparatus 100. The form factor of the auto-darkening apparatus 100 is defined primarily by a housing 120 (a.k.a. a cartridge-like housing 120), which houses the internal components of the apparatus 100. As shown in FIG. 1A, FIG. 1B, and FIG. 1C, the auto-darkening apparatus 100 has a sensitivity adjustment 102, a shade adjustment 104, and a delay adjustment 106. Such types of ADF lens adjustments are known in the art. The auto-darkening apparatus 100 also has two magnifying lens adjustments 108 and 110, each providing a continuous adjustment of magnification (one for each eye of the user). The various adjustments 102, 104, 106, 108, and 110 are user adjustable and may include, for example, any of knobs, dials, switches, gears, springs, and thumb wheels. Other forms of the adjustments may be possible as well, in accordance with other embodiments.

Figure 2:
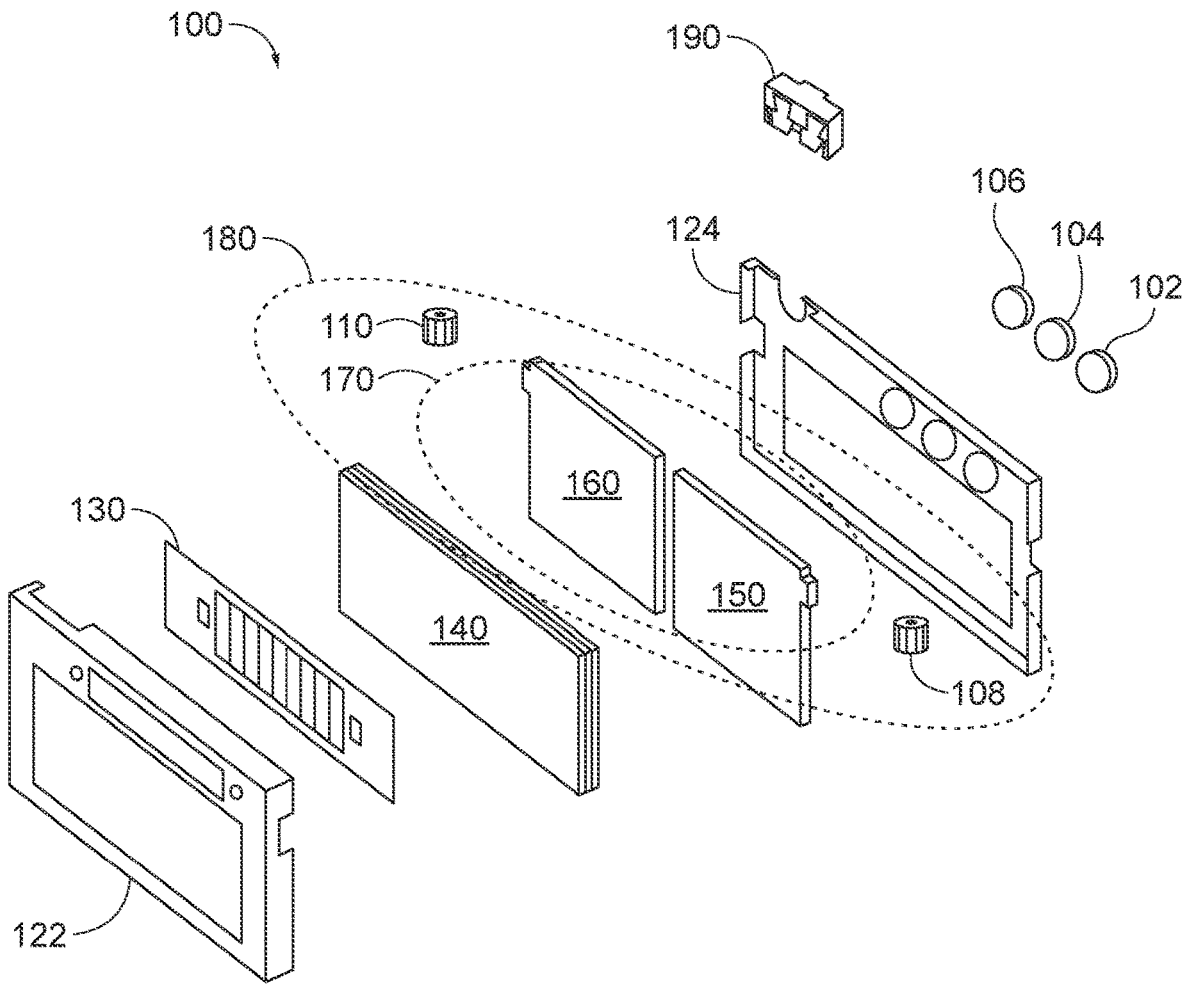
FIG. 2 illustrates an exploded view of the auto-darkening apparatus of FIG. 1.

FIG. 2 illustrates an exploded view of the auto-darkening apparatus 100 of FIG. 1. In addition to the adjustments 102, 104, 106, 108, and 110 discussed above herein, the auto-darkening apparatus 100 also includes a front housing 122 and a rear housing 124 which come together to form a single housing or cartridge 120 (e.g., see FIG. 1B and FIG. 1C). Integrated within the housing 120 is a controller 130, a liquid crystal display (LCD) stack 140 (a.k.a. an ADF lens assembly 140), a left magnifying lens 150 and a right magnifying lens 160 (a.k.a. an optical lens configuration 170 as delineated by a dotted oval in FIG. 2). The magnifying lenses 150 and 160 (the optical lens configuration 170), along with the two magnifying lens adjustments 108 and 110, make up a magnification assembly 180, as delineated by another dotted oval in FIG. 2. The auto-darkening apparatus 100 also includes a battery clip 190 for holding a battery used to power the apparatus 100. The ordering of the primary components of the auto-darkening apparatus 100 are (from front to rear) the front housing 122, the controller 130, the ADF lens assembly 140, the magnification assembly 180, and the rear housing 124.

Figure 8:
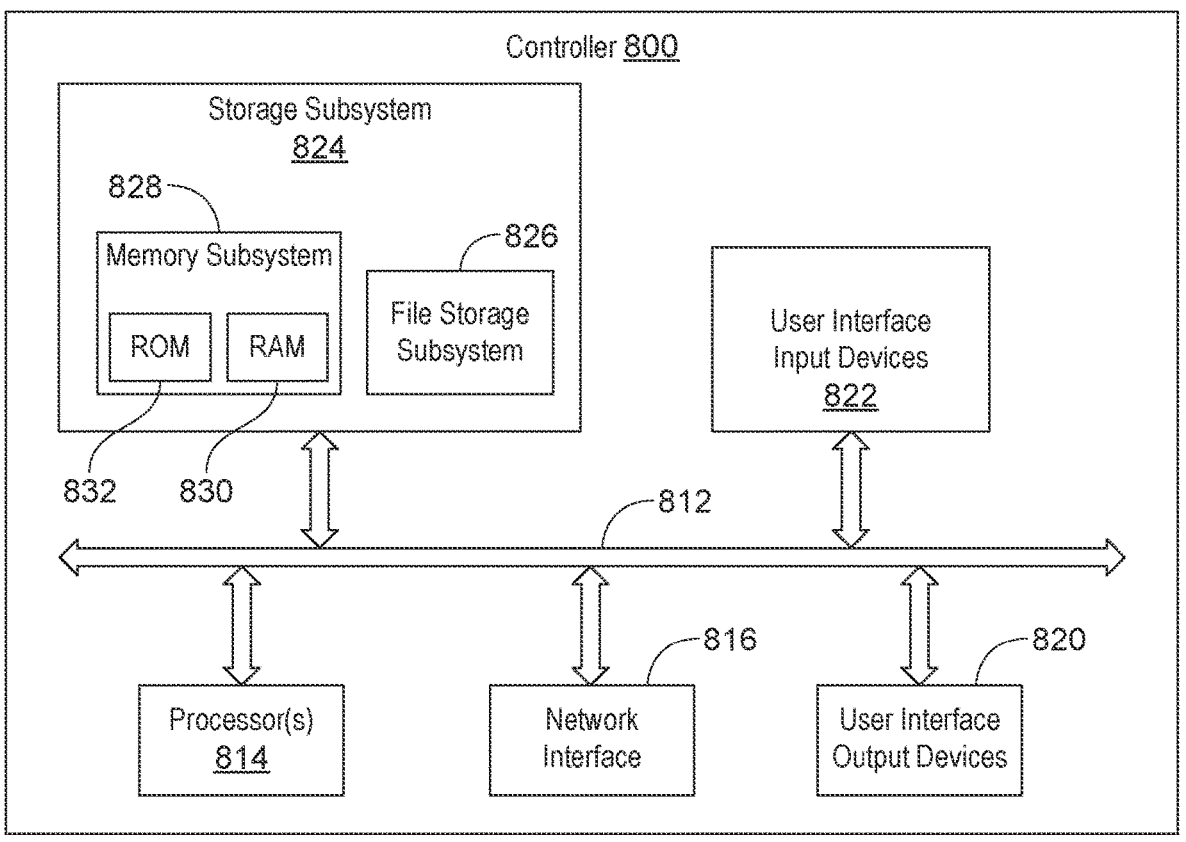
FIG. 8 illustrates a block diagram of an example embodiment of a controller that can be used, for example, as the controller in the auto-darkening apparatus of FIG. 2, or as the controller in the auto-darkening apparatus of FIG. 4.

The controller 130 controls much of the functionality of the auto-darkening apparatus 100 and may be implemented on a printed circuit board (PCB). FIG. 8 herein discusses one embodiment of a controller 800 which may be used as the controller 130. Certain functionality controlled by the controller 130 includes switching of the ADF lens assembly 140 between an un-darkened state and a darkened state (e.g., in response to light from an arc being formed or extinguished between a welding electrode and a work piece during a welding process) and the setting of the sensitivity, the shade, and the delay via the sensitivity adjustment 102, the shade adjustment 104, and the delay adjustment 106 respectively, as selected by the user. The ADF lens assembly 140 may include various layers of LCD lenses and polarization filters, for example, as discussed in U.S. Pat. Nos. 5,825,441, 6,097,451, and 7,477,330 which are incorporated herein by reference. The front housing 122 and the rear housing 124 are largely molded plastic components, in accordance with one embodiment.

The magnifying lenses 150 and 160 of the magnification assembly 180 are optical lenses (e.g., convex optical lenses of a thin lens design) made of glass, in accordance with one embodiment. In some other embodiments, the magnifying lenses 150 and 160 are optical lenses made of a polymer material. Depending on the optical design, the optical lenses may be of various types (e.g., convex, biconvex, plano-convex, positive meniscus, negative meniscus, concave, biconcave, plano-concave, a thin lens design, a thick lens design). In some embodiments, the magnifying lenses 150 and 160 may each include a multiple optical lens design (e.g., having two or more optical lenses arranged with respect to each other to provide desired optical properties). A multiple optical lens design may allow for adjustment of a focal length of the overall magnifying lens, for example. Furthermore, some magnifying lens designs may include prisms used to, for example, rotate or flip the image perceived by the user.

In the exploded configuration of FIG. 2, the magnifying lenses 150 and 160 are located next to each other and behind the ADF lens assembly 140. Each magnifying lens 150 and 160 accommodates a separate eye of the user. The magnification assembly 180 is configured to provide magnification of light coming through the ADF lens assembly 140 such that the magnification is continuously user-adjustable from a defined lower level of magnification (e.g., 1× or no magnification) to a defined upper level of magnification (e.g., 2×, 3×, or 4× magnification). The level of magnification is mechanically adjustable, via the magnifying lens adjustments 108 and 110, in a continuous manner from the defined lower level of magnification to the defined upper level of magnification, and back again.

In one embodiment, the magnification assembly 180 includes the optical lens configuration 170 (having magnifying lenses 150 and 160) and the magnifying lens adjustments 108 and 110. The magnifying lens adjustments 108 and 110 are configured to be manipulated by a user to mechanically adjust one or more of an angle, a position, or a focal length of the respective lenses 150 and 160 within the housing 120, resulting in an adjustment of a level of magnification with respect to light coming through the ADF lens assembly 140. For example, in accordance with one embodiment, each of the magnifying lenses 150 and 160 can be rotated (angled) toward or away from the user's eyes. Rotating the lenses toward the user results in greater magnification, whereas rotating the lenses away from the user results in less magnification. Changing the angle by merely tenths of a degree can significantly change the level of magnification.

In accordance with one embodiment, each of the magnifying lens adjustments 108 and 110 include a rotatable thumb wheel, a set of miniature gears, and a set of miniature springs configured to manipulate the magnifying lenses 150 and 160 to affect mechanical adjustment of angle, position, and/or focal length. Other embodiments of the magnifying lens adjustments 108 and 110 are possible as well, for mechanically manipulating the magnifying lenses 150 and 160. For example, in accordance with one embodiment, the magnifying lenses 150 and 160 are made of a flexible polymer material, and the magnifying lens adjustments 108 and 110 are configured to bend or change the shape of the respective magnifying lenses 150 and 160, resulting in a change of focal length and, therefore, a level of magnification of the magnifying lenses 150 and 160.

Figure 3:
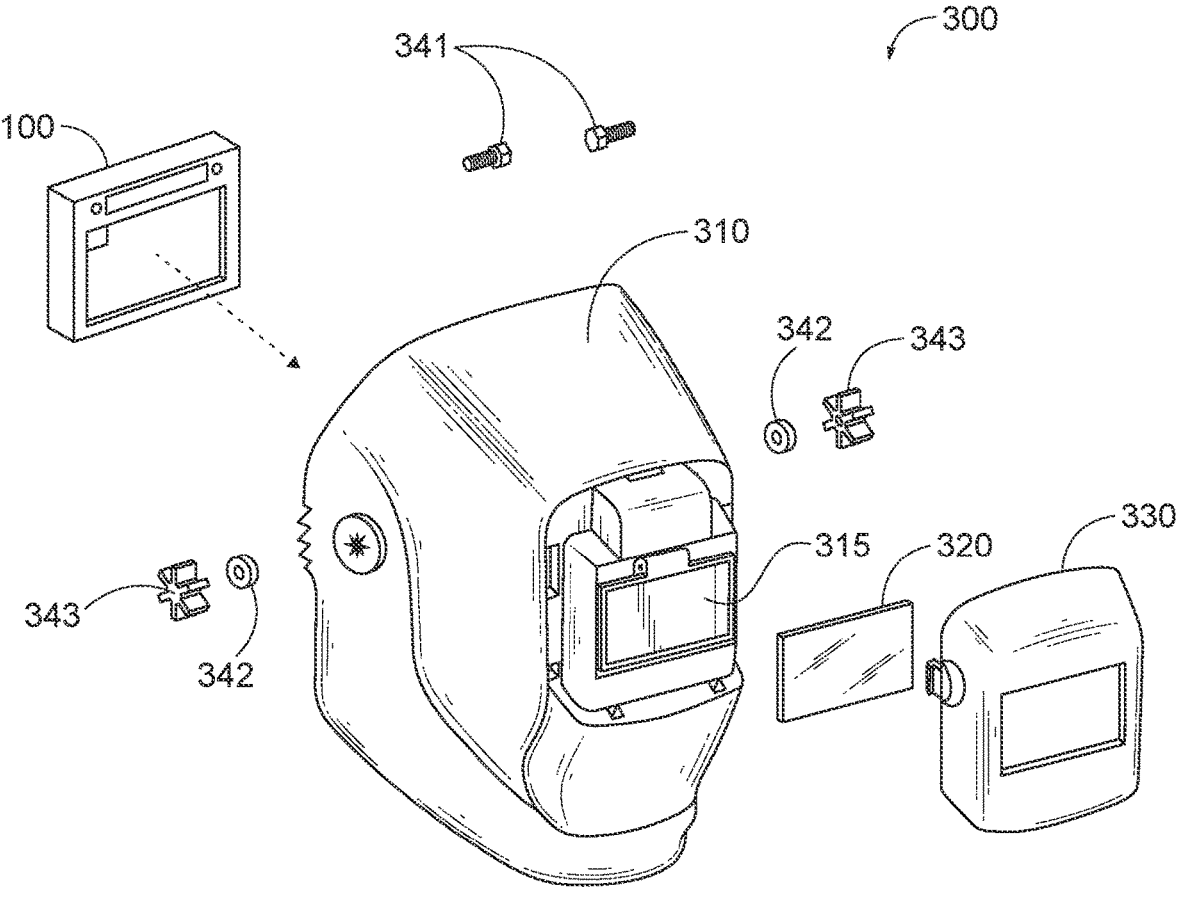
FIG. 3 illustrates an exploded view of one embodiment of a welding helmet that is configured to have the auto-darkening apparatus of FIG. 1A, FIG. 1i, FIG. 1C, and FIG. 2 installed therein.

FIG. 3 illustrates an exploded view of one embodiment of a welding helmet 300 that is configured to have the auto-darkening apparatus 100 of FIG. 1A, FIG. 1B, FIG. 1C, and FIG. 2 installed therein. The welding helmet 300 includes a shell 310, a viewing window 315 (e.g., an open viewing window), a spatter shield 320, a front bezel 330, and headgear mounting hardware 341, 342, 343 for a headgear (not shown). The spatter shield 320 and the front bezel 330 are installed from the front of the shell 310. The auto-darkening apparatus 100 is installed from the rear of the shell 310, similar to a conventional auto-darkening filter. However, unlike a conventional auto-darkening filter, the auto-darkening apparatus 100 has the integrated magnification assembly 180, providing a continuously adjustable magnification capability as described herein. U.S. Pat. No. 9,889,045 discusses various examples of welding helmet configurations and is incorporated herein by reference.

Figure 4:
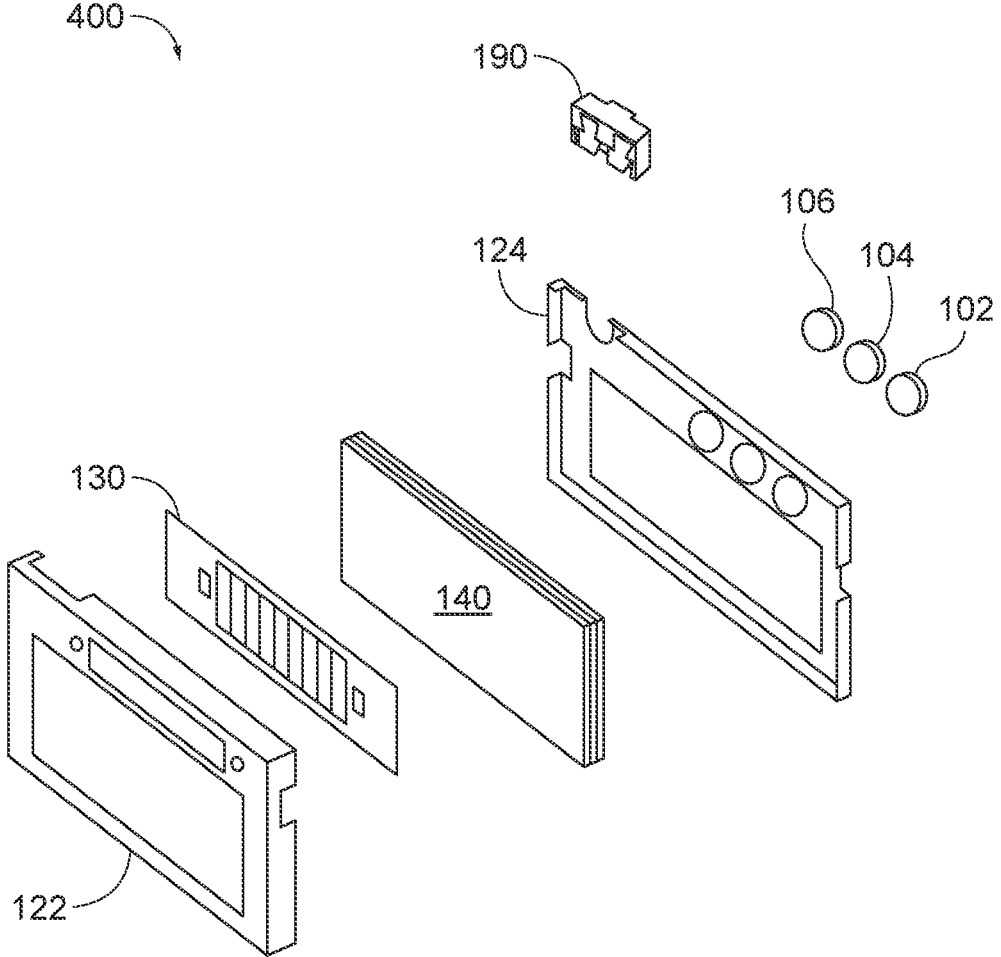
FIG. 4 illustrates an exploded view of one embodiment of an auto-darkening apparatus for supporting welding performed by a human welder.
Figure 5:
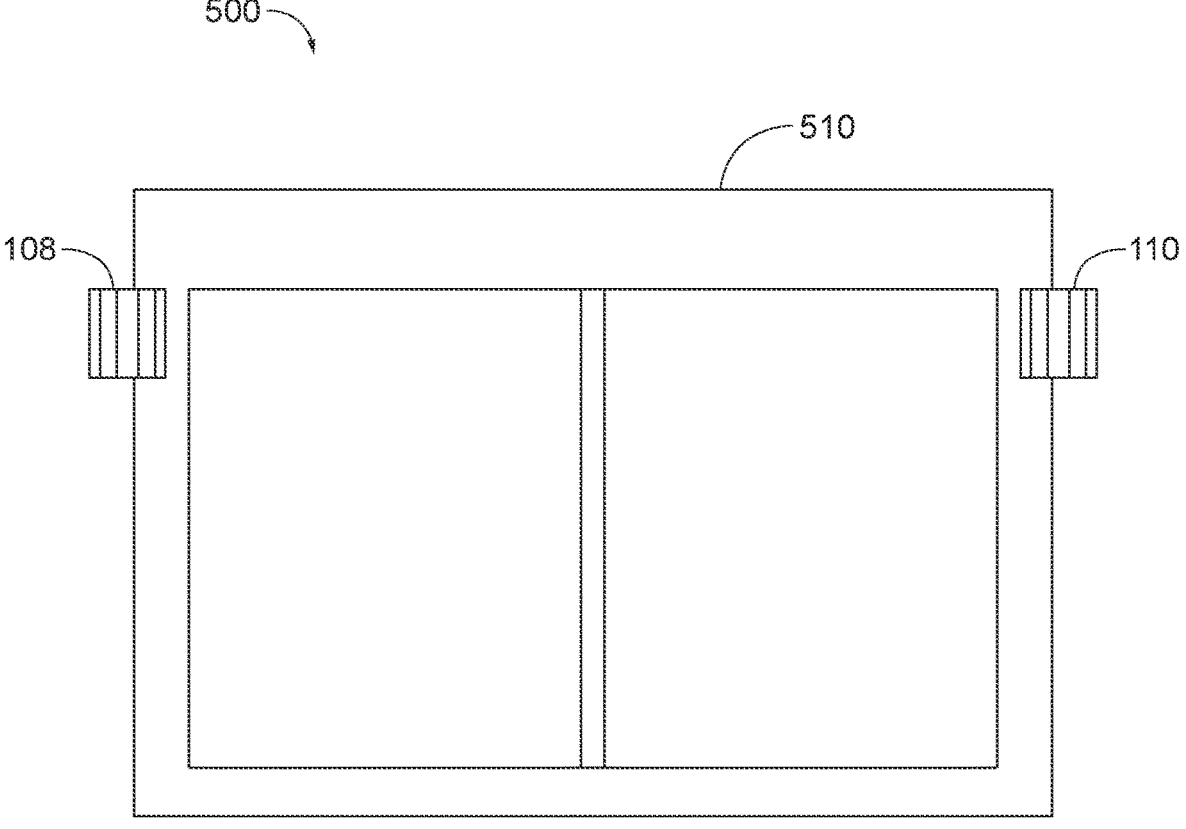
FIG. 5 illustrates one embodiment of a magnifying apparatus having a magnification assembly integrated therein, for supporting welding performed by a human welder, which is housed in a separate housing from that of the auto-darkening apparatus of FIG. 4.
Figure 6A:
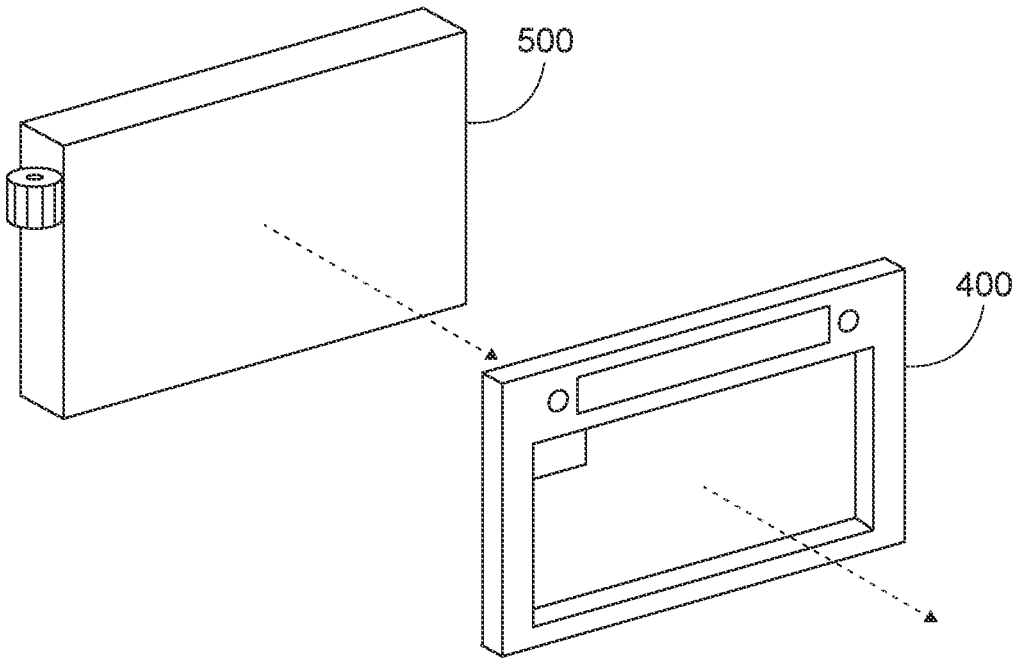
FIG. 6A illustrates the relationship of the auto-darkening apparatus of FIG. 4 with respect to the magnifying apparatus of FIG. 5.
Figure 6B:
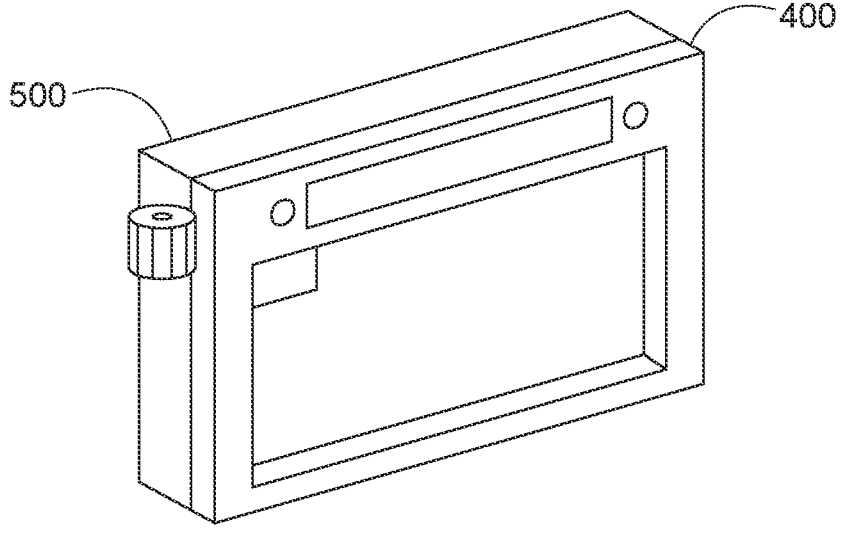
FIG. 6B illustrates the magnifying apparatus of FIG. 5 positioned directly behind and abutting the auto-darkening apparatus of FIG. 4 as they would be when installed in a welding helmet.

In other embodiments, the magnification assembly 180 may be in a different housing from that of the auto-darkening elements. For example, FIG. 4 illustrates an exploded view of one embodiment of an auto-darkening apparatus 400 for supporting welding performed by a human welder. The elements of the auto-darkening apparatus 400 are similar to those of the auto-darkening apparatus 100 of FIG. 2, except that the auto-darkening apparatus 400 does not include the magnification assembly 180. Instead, FIG. 5 illustrates one embodiment of a magnifying apparatus 500 having the magnification assembly 180 integrated therein, for supporting welding performed by a human welder, which is housed in a separate housing 510 from that of the auto-darkening apparatus 400. Various embodiments of the magnifying apparatus 500 operate similarly to the various embodiments of the magnification assembly 180 discussed herein. The magnifying apparatus 500 is a largely mechanical apparatus and does not require a controller 130 or a battery, as does the auto-darkening apparatus 400. As a result FIG. 6A illustrates the relationship of the auto-darkening apparatus 400 of FIG. 4 with respect to the magnifying apparatus 500 of FIG. 5. FIG. 6B illustrates the magnifying apparatus 500 of FIG. 5 positioned directly behind and abutting the auto-darkening apparatus 400 of FIG. 4 as it would be when installed in a welding helmet.

Figure 7:
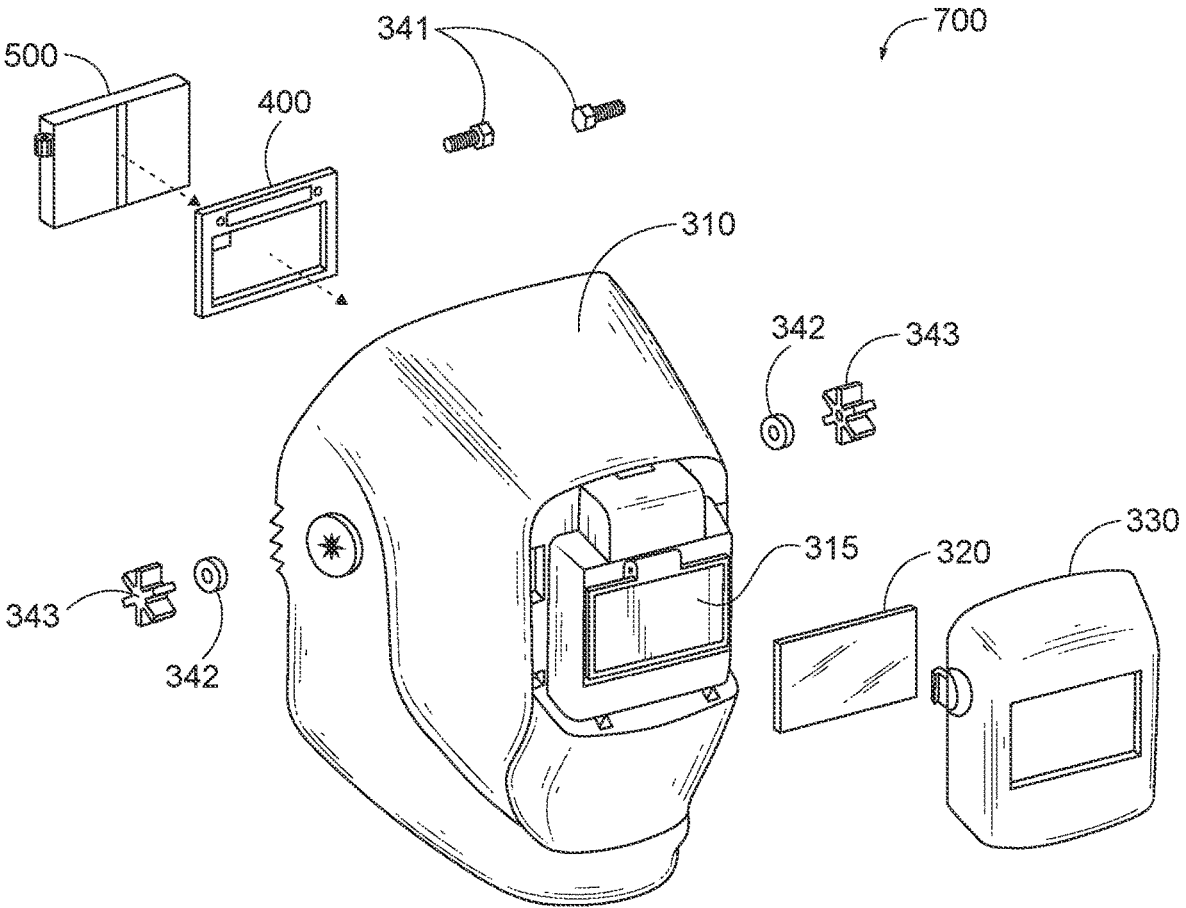
FIG. 7 illustrates an exploded view of one embodiment of a welding helmet that is configured to have the auto-darkening apparatus and the magnifying apparatus of FIG. 6A installed therein.

FIG. 7 illustrates an exploded view of one embodiment of a welding helmet 700 that is configured to have the auto-darkening apparatus 400 and the magnifying apparatus 500 of FIG. 6A and FIG. 6B installed therein. The welding helmet 700 is similar to the welding helmet 300 of FIG. 3, except that the welding helmet 700 is configured for installation of the auto-darkening apparatus 400 and the magnifying apparatus 500, instead of the auto-darkening apparatus 100. The auto-darkening apparatus 400 is installed first, from the rear of the shell 310, followed by installation of the magnifying apparatus 500. However, the resultant darkening and magnification capabilities are essentially the same in both of the welding helmets 300 and 700.

FIG. 8 illustrates a block diagram of an example embodiment of a controller 800 that can be used, for example, as the controller 130 in the auto-darkening apparatus 100 of FIG. 2, or as the controller 130 in the auto-darkening apparatus 400 of FIG. 4. Referring to FIG. 8, the controller 800 includes at least one processor 814 (e.g., a microprocessor) which communicates with a number of other components via a bus subsystem 812. These other devices may include a storage subsystem 824, including, for example, a memory subsystem 828 and a file storage subsystem 826, user interface input devices 822, user interface output devices 820, and a network interface subsystem 816. The input and output devices allow user interaction with the controller 800. Network interface subsystem 816 provides an interface to outside networks and is coupled to corresponding interface devices in yet other devices.

User interface input devices 822 may include audio input devices such as voice recognition systems and microphones, or wireless communication devices (e.g., Bluetooth® or Wi-Fi devices), for example. In general, use of the term "input device" is intended to include all possible types of devices and ways to input information into the controller 800 from the user or onto a communication network, which fit within the form factor of an auto-darkening apparatus. User interface output devices 820 may include audio output devices such as speakers, or wireless communication devices (e.g., Bluetooth® or Wi-Fi devices), for example. In general, use of the term "output device" is intended to include all possible types of devices and ways to output information from the controller 800 to the user or to another machine or computer system, which fit within the form factor of an auto-darkening apparatus.

Storage subsystem 824 stores programming and data constructs that provide some of the functionality described herein. For example, computer-executable instructions and data are generally executed by processor 814 alone or in combination with other processors. Memory 828 used in the storage subsystem 824 can include a number of memories including a main random access memory (RAM) 830 for storage of instructions and data during program execution and a read only memory (ROM) 832 in which fixed instructions are stored. A file storage subsystem 826 can provide persistent storage for program and data files and may include removable media such as a removable media cartridge, for example. The computer-executable instructions and data implementing the functionality of certain embodiments may be stored by file storage subsystem 826 in the storage subsystem 824, or in other machines accessible by the processor(s) 814 (e.g., via wireless communication means).

Bus subsystem 812 provides a mechanism for letting the various components and subsystems of the controller 800 communicate with each other as intended. Although bus subsystem 812 is shown schematically as a single bus, alternative embodiments of the bus subsystem may use multiple buses.

The controller 800 can be of varying types. Due to the ever-changing nature of computing devices and networks, the description of the controller 800 depicted in FIG. 8 is intended only as a specific example for purposes of illustrating some embodiments. Many other configurations of a controller are possible, having more or fewer components than the controller 800 depicted in FIG. 8.

While the disclosed embodiments have been illustrated and described in considerable detail, it is not the intention to restrict or in any way limit the scope of any subsequent appended claims to such detail. It is, of course, not possible to describe every conceivable combination of components or methodologies for purposes of describing the various aspects of the subject matter. Therefore, the disclosure is not limited to the specific details or illustrative examples shown and described. Thus, this disclosure is intended to embrace alterations, modifications, and variations that fall within the scope of subsequent appended claims, which satisfy the statutory subject matter requirements of 35 U.S.C. § 101. The above description of specific embodiments has been given by way of example. From the disclosure given, those skilled in the art will not only understand the general inventive concepts and attendant advantages, but will also find apparent various changes and modifications to the structures and methods disclosed. It is sought, therefore, to cover all such changes and modifications as fall within the spirit and scope of the general inventive concepts, as defined by subsequent appended claims, and equivalents thereof.

What is claimed is:

1. An auto-darkening apparatus for supporting welding performed by a human welder, the auto-darkening apparatus comprising:

a housing configured to be removably installed into a welding helmet, said housing including an ADF lens assembly configured to transition from an un-darkened state to a darkened state in response to light from an arc being formed between a welding electrode and a work piece during a welding process; and a magnification assembly configured to provide magnification of light coming through the ADF lens assembly, wherein the magnification is continuously user-adjustable from a defined lower level of magnification to a defined upper level of magnification, wherein the magnification assembly is configured to be removably attached to the welding helmet, and wherein the magnification assembly includes an optical lens and a magnifying lens adjustment configured to be manipulated by a user to mechanically adjust an angle at which at least a portion of the optical lens is oriented within the housing, resulting in an adjustment of a level of magnification of light coming through the ADF lens assembly as viewed by the user.

2. The apparatus of claim 1, wherein the defined lower level of magnification is a magnification level of 1.

3. The apparatus of claim 1, wherein the defined upper level of magnification is between 1.9 and 4.1.

4. The apparatus of claim 1, wherein the defined upper level of magnification is between 1.4 and 2.1.

5. The apparatus of claim 1, wherein the auto-darkening apparatus is configured to provide user adjustment of at least one of a sensitivity, a shade, and a delay of the ADF lens assembly.

6. A welding helmet for supporting welding performed by a human welder, the welding helmet comprising:

a helmet shell, having a viewing window, configured to be worn on the head of a user;

an ADF lens assembly within a first housing, the ADF lens assembly configured to transition from an un-darkened state to a darkened state in response to light from an arc being formed between a welding electrode and a work piece during a welding process, wherein the first housing is configured to be removably attached to the helmet shell at the viewing window; and a magnification assembly within a second housing, the magnification assembly configured to provide magnification of light coming through the ADF lens assembly, wherein the magnification is continuously user-adjustable from a defined lower level of magnification to a defined upper level of magnification, and wherein the second housing is configured to be removably attached to the helmet shell adjacent to the first housing at the viewing window, and wherein the magnification assembly includes an optical lens and a magnifying lens adjustment configured to be manipulated by a user to mechanically adjust at least one of a focal length of the optical lens or a position of at least a portion of the optical lens within the housing, resulting in an adjustment of a level of magnification of light coming through the ADF lens assembly as viewed by the user.

7. The welding helmet of claim 6, wherein the defined lower level of magnification is a magnification level of 1.

8. The welding helmet of claim 6, wherein the defined upper level of magnification is between 1.9 and 4.1.

9. The welding helmet of claim 6, wherein the defined upper level of magnification is between 1.4 and 2.1.

10. The welding helmet of claim 6, wherein the welding helmet is configured to provide user adjustment of at least one of a sensitivity, a shade, and a delay of the ADF lens assembly.

11. An auto-darkening apparatus for supporting welding performed by a human welder, the auto-darkening apparatus comprising:

a housing configured to be removably installed into a welding helmet, said housing including an ADF lens assembly configured to transition from an un-darkened state to a darkened state in response to light from an arc being formed between a welding electrode and a work piece during a welding process; and a magnification assembly configured to provide magnification of light coming through the ADF lens assembly, wherein the magnification is continuously user-adjustable from a defined lower level of magnification to a defined upper level of magnification, wherein the magnification assembly is configured to be removably attached to the welding helmet, and wherein the magnification assembly includes an optical lens and a magnifying lens adjustment configured to be manipulated by a user to mechanically adjust at least one of a focal length of the optical lens or a position of at least a portion of the optical lens within the housing, resulting in an adjustment of a level of magnification of light coming through the ADF lens assembly as viewed by the user.

\* \* \* \* \*